United States Patent
Mueller

(10) Patent No.: US 11,144,447 B2
(45) Date of Patent: Oct. 12, 2021

(54) DEVICE FOR PERFORMING AT LEAST ONE MEDICAL ACTION AT A HUMAN OR ANIMAL BODY VIA DEVICE OVER MEMORY CLEANING CALLED BY WEAR LEVELING

(71) Applicant: Roche Diabetes Care, Inc., Indianapolis, IN (US)

(72) Inventor: Michael Mueller, Mannheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 248 days.

(21) Appl. No.: 16/349,330

(22) PCT Filed: Dec. 8, 2017

(86) PCT No.: PCT/EP2017/081952
§ 371 (c)(1),
(2) Date: May 13, 2019

(87) PCT Pub. No.: WO2018/104496
PCT Pub. Date: Jun. 14, 2018

(65) Prior Publication Data
US 2019/0385737 A1 Dec. 19, 2019

(30) Foreign Application Priority Data
Dec. 9, 2016 (EP) ..................................... 16203132

(51) Int. Cl.
| | |
|---|---|
| *G06F 12/02* | (2006.01) |
| *G16H 40/63* | (2018.01) |
| *G06F 3/06* | (2006.01) |
| *A61B 5/335* | (2021.01) |

(52) U.S. Cl.
CPC .......... *G06F 12/0246* (2013.01); *A61B 5/335* (2021.01); *G06F 3/0679* (2013.01); *G16H 40/63* (2018.01); *G06F 2212/7211* (2013.01)

(58) Field of Classification Search
CPC ............... G06F 12/0246; G06F 3/0679; G06F 2212/7211; G16H 40/63; A61B 5/335
See application file for complete search history.

(56) References Cited

U.S. PATENT DOCUMENTS 9,292,432 B2 * 3/2016 Chu .................... G06F 12/0246
2003/0163633 A1 8/2003 Aasheim et al.

FOREIGN PATENT DOCUMENTS

WO WO 2007/127879 1/2007

* cited by examiner

*Primary Examiner* — Tammara R Peyton
(74) *Attorney, Agent, or Firm* — Woodard, Emhardt, Henry, Reeves & Wagner, LLP

(57) ABSTRACT

The invention relates to a device (100) for performing at least one medical action at a human or animal body; wherein the device (100) comprises an energy source (107) and a computer (103); wherein the computer (103)
 a) comprises a first erasable non-volatile memory (104), and
 b) is configured for performing at least one application, the application being configured
  i) to control the medical action, and
  ii) to prioritize the medical action over a memory cleaning called by a wear leveling.
Furthermore, the invention relates to a process, comprising operating the device (100) in consecutive cycles or tasks; to a use of a wear leveling algorithm and a prioritizing algorithm; and to a use of the device (100) in a treatment of a diabetes mellitus.

14 Claims, 3 Drawing Sheets

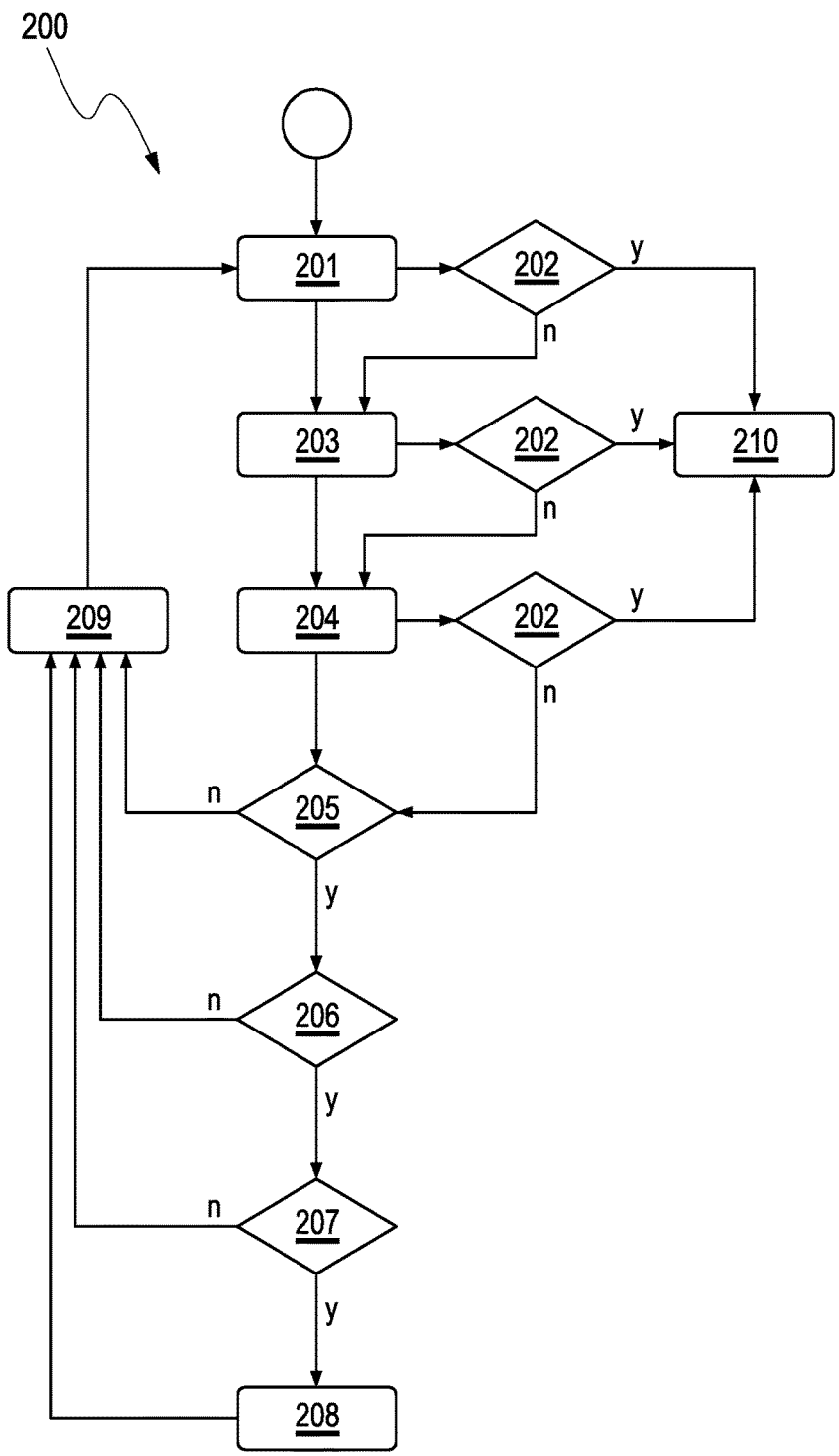
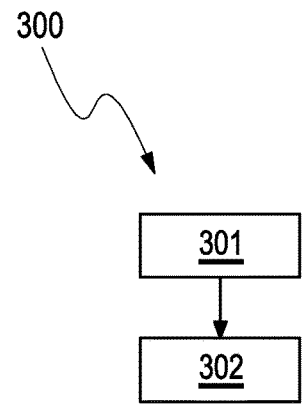
Fig. 2
Fig. 3

DEVICE FOR PERFORMING AT LEAST ONE MEDICAL ACTION AT A HUMAN OR ANIMAL BODY VIA DEVICE OVER MEMORY CLEANING CALLED BY WEAR LEVELING

FIELD OF THE INVENTION

The invention relates to a device for performing at least one medical action at a human or animal body; wherein the device comprises an energy source and a computer; wherein the computer
  a) comprises a first erasable non-volatile memory, and
  b) is configured for performing at least one application, the application being configured
    i) to control the medical action, and
    ii) to prioritize the medical action over a memory cleaning called by a wear leveling.

Furthermore, the invention relates to a process, comprising operating the device in consecutive cycles; to a use of a wear leveling algorithm and a prioritizing algorithm; and to a use of the device in a treatment of diabetes.

RELATED ART

Flash memories in general allow for only a limited number of write and erase cycles. Typically, a flash memory includes floating gate transistors (FGMOS) or charge trap components. Therein, FGMOS are field-effect transistors having two gates. One of these is an electrically isolated floating gate, to which a certain amount of electrical charge may be applied. Applying this amount of electrical charge to the floating gate corresponds to setting the value of the gate to 0. In turn, removing the charge from the floating gate corresponds to setting its value to 1. Therein, writing into the memory corresponds to setting the value of at least one cell to 0, wherein erasing involves setting the value to 1. After a certain number of such write and erase cycles, the layers which electrically isolate the floating gates of the field-effect transistors suffer from wear. Due to material defects in the isolating layers electrical charges may be trapped which produces undefined reading errors. Such errors typically occur after about several thousand writings into and erasing actions from the flash memory.

Further, it is generally known that erasing data from a flash memory may only be effected per full page, not per single cell. Typical pages consist of 512, 2048 or 4096 cells. However, writing into the flash memory may be effected per single cell. As the allowable number of write and erase cycles for each cell is limited and erasing can only be performed per full page of the flash memory, as few as possible erase cycles should be performed in order to increase the lifetime of the flash memory. Further, the write cycles should be distributed over the cells of the flash memory in order to prevent single cells from suffering a higher degree of wear than other cells. This is because, the cell which suffers the highest degree of wear (wear level) determines the lifetime of the flash memory as it may start to produce errors much earlier than other cells with lower wear levels. Therefore, in the prior art complex algorithms have been developed to distribute the read and write accesses over the cells of the flash memory such that the wear is evenly distributed. Such algorithms are called wear leveling algorithms. Typically a wear level controller is located on the memory chip in order to control the read and write cycles. By applying such a wear leveling, the allowed number of write and erase cycles of the flash memory may be increased by a so called wear leveling factor. Hence, the wear leveling factor is a parameter which characterized prolonging of the service life of the flash memory by applying wear leveling.

Using a flash memory in a medical device, such as an insulin pump or a continuous glucose sensor, the lifetime of the flash memory puts an upper limit to the lifetime of the medical device. No need to mention that an as high as possible lifetime of the medical device is desired. Therefore, applying wear leveling to the flash memory of the medical device is desirable. However, on such a medical device typically a lot of time critical functions, i.e. medical functions, have to be performed. This puts additional requirements to the performance of the flash memory. For example, in the prior art, memory access cycles to a flash memory involving wear leveling are rather slow and time consuming. Further, these memory access cycles are energy consuming. Therefore, it is desirable to perform erase steps only when no time critical action is due. Further, a wear leveling process of a medical device of the prior art involves reserving regions of the flash memory for various operational scenarios which include tasks of particular importance, i.e. medical tasks. Such a wear leveling comes with the drawback of blocking these regions of memory for any further use. Further, wear leveling algorithms of the prior art do not allow for a predictable real time behaviour within an embedded system. In particular, the time needed for read and/or write operations may not be predictable. Moreover, wear leveling algorithms of the prior art do not allow for a predictable energy consumption within an embedded system. Further, a prior art medical device-flash memory with wear leveling does not allow for an in situ error detection and/or error correction.

Problem to be Solved

It is therefore an objective of the present invention to provide a medical device with a flash memory which at least partially avoids the above-mentioned shortcomings of known flash memory devices. Specifically, a performance of the medical device shall be improved as compared to known medical flash memory devices.

SUMMARY OF THE INVENTION

This problem is solved by a device for performing at least one medical action at a human or animal body; by a process, comprising operating this device in consecutive cycles; by a use of a wear leveling algorithm and a prioritizing algorithm; and by a use of the device in a treatment of a diabetes, each with the features of the independent claims. Preferred embodiments, which might be realized in an isolated fashion or in any arbitrary combination are listed in the dependent claims.

Specifically, a medical device with a flash memory may be provided, wherein a lifetime of the medical device shall be increased.

Further, the medical device may show an improved level of reliability or operational safety or both. Further, the medical device may have a flash memory, wherein a capacity of the flash memory can be used as efficiently as possible. In this context, the medical device may need a lower capacity of the flash memory in order to fulfill the same tasks. Further, costs for flash memory capacity of the medical device may be reduced. A reading of the flash memory may be faster and/or more predictable. A wear leveling factor of the flash memory may be predictable. A timing or an energy consumption behavior of the medical device or both may be predictable. The timing or the energy consumption behavior of the medical device or both may be predictable during a clean-up phase of the flash memory, more preferably in real-time. The medical device may comprise as few electronic components as possible. The medical device may not comprise a wear leveling controller, at all. Further, a process for operating the medical device may be provided.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "preferably", "more preferably", "particularly", "more particularly", "specifically", "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

As far as this document relates to a "first" entity or a "second" entity or a "further" entity, the terms "first", "second" and "further" are chosen as a matter of nomenclature only. The presence of a "first" entity does not imply the presence of a "second" or "further" entity. The presence of a "second" entity does not imply the presence of a "first" entity. Moreover, the terms "first", "second" and "further" are used to distinguish several entities without implying any order of these entities.

Features which are preferred according to an embodiment of a category of the invention are as well preferred for corresponding components or entities of another category of the invention. Therein, components or entities may be corresponding to each other in terms of their name or function according to the invention.

In a first aspect of the present invention, a device for performing at least one medical action at a human or animal body is disclosed. As used herein, a medical action generally may refer to an arbitrary action selected from the group consisting of a diagnostic action and a therapeutic action. As an example, the medical action may be or may comprise the determination of an analyte, such as an analyte in a body fluid and/or in a body tissue. Additionally or alternatively, the medical action may be or may comprise a medication, such as a medication of at least one drug.

The device comprises an energy source and a computer. The energy source, as an example, may be or may comprise at least one energy storage device, such as at least one of a battery, an accumulator and a supercap. Additionally or alternatively, the energy source may comprise an external energy source, such as an external plug. A battery, as an example, may be or may comprise a rechargeable battery. Additionally or alternatively, the energy source may be or comprise a photovoltaic cell.

The computer may comprise a processor, such as a central processing unit (CPU). The processor may be comprised by a single integrated circuit. In this case the processor may be referred to as microprocessor. Further, the computer may comprise a microcontroller.

Therein, the microcontroller may be an integrated circuit which may comprise a processor, a memory and one or more peripherals. Therein, the peripheral may be programmable. Further, the peripheral may be an input peripheral or an output peripheral or both. Further, the computer comprises a first erasable non-volatile memory, and the computer is configured for performing at least one application. As used herein, an application may generally refer to the capability of performing one or more processes, such as one or more algorithms. As an example, the application may be suited to control the above-mentioned one or more medical actions and/or at least one part thereof. The application may control one or more of a starting of the medical action, a duration of the medical action, a frequency of performing the medical action and a dosage of the medical action or a combination of at least two thereof.

Therein, the application may be stored in a data storage medium of the computer, wherein the data storage medium is readable by the processor. The application may fully or partially be embodied in software. Thus, as an example, the computer, specifically the storage medium, may store one or more of commands, software, and algorithm or code which, when read by our loaded into the processor are suited to make the processor perform the application or a part thereof. Thus, the application may be or may comprise software, such as a computer program.

The application is configured to control the medical action, and to prioritize the medical action over a memory cleaning called by a wear leveling. Therein, the memory cleaning may be a cleaning of the first erasable non-volatile memory.

As used herein, the term "to call" or "to be called" may generally refer to an instance of the computer; e.g. the processor, the application or an algorithm which is implemented in the application; communicating that a particular action is due, i.e. needs to be performed. If an action is called, this may not instantly cause performing the action. Instead, a calling of an action may lead to a checking of further requirements for performing the action. This checking of further requirements may be performed by an instance of the computer which is different from the instance which called the action. If these further requirements are fulfilled, the action may be started.

Generally, the term "wear leveling" may refer to a process or to instructions involving a distribution of accesses to regions of a plurality of regions of the first erasable non-volatile memory over this plurality of regions. Therein, the regions may for example be data blocks. In this context, accesses may be read accesses, write accesses or erase accesses or combinations of those.

The term memory cleaning generally may refer to an action which comprises an erasing of regions of the first erasable non-volatile memory. These regions may be data blocks, in particular invalid data blocks. The memory cleaning may further refer to an erasing of all invalid data blocks of a particular data region of the first erasable non-volatile memory.

The application may be programmable. Herein, the programmable application may be adjusted in terms of one or more of: a starting of the medical action, a duration of the medical action, a frequency of performing the medical action and a dosage of the medical action or a combination of at least two thereof. Programming the application may be performed by manual interaction with the device or by means of a remote controller or both. Specifically in case of a remote controller, the device may comprise a receiving unit for receiving control signals from the remote controller. Therein, the receiving unit may be configured to receive one selected from the group consisting of radio signals, infrared signals and wire bound signals or a combination of at least two thereof.

The device specifically may be or may comprise a medical device. A medical action specifically may be or may comprise a treatment of a disease or a malfunction or both in each case of a human or animal body. A further medical action may be a measurement of at least one diagnostic parameter of a human or animal body.

In a further aspect of the invention, the wear leveling is called by a wear leveling algorithm, wherein the wear leveling algorithm is comprised by the application. The wear leveling specifically may be or may comprise a dynamic wear leveling or a static wear leveling or both. The wear leveling algorithm specifically may be implemented into the application. The wear leveling algorithm specifically may be comprised by a source code of the application.

Further, the prioritizing may be implemented in a prioritizing algorithm, wherein the prioritizing algorithm is comprised by the application. The prioritizing algorithm specifically may be implemented into the application. The prioritizing algorithm, as an example, may be comprised by the source code of the application. As used herein, the prioritizing algorithm may generally refer to an instruction or a sequence of instructions which monitor an availability of a resource and affect a chronological ordering of actions that make use of this resource or resources. Therein, the resource may for example be time or energy. In this context, the prioritizing algorithm may chronologically prefer one action over another which may involve postponing the other action.

Moreover, the application may be further configured to prioritize a securing of a communication connection of the device over the memory cleaning called by the wear leveling. The communication connection specifically may be or may comprise a wireless communication connection. This communication connection may be a communication connection between the device and the abovementioned remote controller. The securing of the communication connection may specifically be or may comprise checking if the communication connection is intact or trying to establish or re-establish the communication connection or communicating an error message or combinations of those.

The device specifically may be designed to be operated in cycles or tasks or both. Therein, specifically, the application may be designed for operating the device in cycles or tasks or both. Therein, the cycles may be consecutive cycles and the tasks may be consecutive tasks.

Each cycle has one or both of a duration or a portion of energy from the energy source available for the cycle. Therein, the application may determine this duration of cycles and/or portion of energy available for each cycle. Therefore, the duration of each cycle may be predetermined, such as by the application. Further, the application is designed to prioritize the medical action over the memory cleaning called by the wear leveling in terms of one or both of a duration of a cycle or a portion of energy available for a cycle. This means particularly that the application may ensure that enough time and/or energy is available in each cycle, in which the medical action is to be performed, to perform this medical action. Only if enough time and/or energy are available in the cycle which is not needed to perform the medical action, the memory cleaning according to the wear leveling may be performed.

A task may be any action that the device is designed for to perform, such as the medical action, the memory cleaning or a communication task. Further, each task may have one or both of a duration or a portion of energy needed to perform the task. The duration of each task may be predetermined, such as by the application. For example, the memory cleaning may be a time deterministic task, i.e. a task which has a predetermined duration. Further, the application is designed to prioritize the medical action over the memory cleaning called by the wear leveling in terms of one or both of a duration of a task or a portion of energy needed for a task.

In the context of the device being operated in cycles, it is further possible for the application to be designed to prioritize the medical action over the memory cleaning called by the wear leveling in terms of one or both of a duration of a cycle or a portion of energy available for a cycle. This may imply that the application may ensure that enough time and/or energy is available in each cycle, in which the medical action is to be performed, to perform this medical action. Only if enough time and/or energy are available in the cycle which is not needed to perform the medical action, the memory cleaning according to the wear leveling is started.

The portion of energy may be provided by an energy portioning component, which is comprised by the device. Therein, the energy portioning component is designed to be charged by the energy source. For example, the energy portioning component may be designed to be charged with the portion of energy of a cycle from the energy source. The energy portioning component specifically may be or may comprise a capacitor.

The first erasable non-volatile memory specifically may comprise a data storage region, comprising a first set of valid data blocks, and a block allocation table, comprising a valid allocation entry for each valid data block of the first set. The data storage region may further comprise invalid data blocks and/or free data blocks. Rewriting a valid data block of the first set according to the wear leveling preferably comprises
  a) invalidating the valid allocation entry in the block allocation table for the valid data block to be rewritten;
  b) writing a further valid allocation entry for a further valid data block of the first set into a free allocation entry of the block allocation table;
  c) invalidating the valid data block of the first set to be rewritten, thereby obtaining an invalid data block of the first set; and
  d) writing the further valid data block of the first set into a free data block of the data storage region.

The term data block may refer to a sequence of bytes or bits, usually containing some whole number of records, having a maximum length, a block size. Data thus structured are said to be blocked. The process of putting data into blocks is called blocking, while deblocking is the process of extracting data from blocks. The data storage region may refer to a plurality of data blocks of a memory. Data which is written into the first erasable non-volatile memory according to the wear leveling may be written into the data storage region. The block allocation table as used herein may be a data structure in the first erasable non-volatile memory used to track data blocks that are considered valid.

If one or both of the following conditions is/are fulfilled, the memory cleaning is called by the wear leveling: less than a minimum number of free data blocks is available in the data storage region for step d); less than a minimum number of free allocation entries is available in the block allocation table for step b). In particular, the memory cleaning may be called if one or both of the following conditions is/are fulfilled: no free data block is available in the data storage region for step d); no free allocation entry is available in the block allocation table for step b). The memory cleaning may comprise erasing a plurality of invalid allocation entries of the block allocation table or a plurality of invalid data blocks of the data storage region or both. In particular, the memory cleaning may comprise erasing all invalid allocation entries of the block allocation table or all invalid data blocks of the data storage region or both. Erasing an invalid data block specifically may comprise setting this invalid data block to 1, thereby obtaining a free data block. Erasing an invalid allocation entry specifically may comprise setting this invalid allocation entry to 1, thereby obtaining a free allocation entry. However, as noted above erasing data from a flash memory may typically only be effected per full page, such as per full page of the data storage region or per full per of the block allocation table. Invalidating a valid data block specifically may comprise setting this valid data block to 0, thereby obtaining an invalid data block. Invalidating a valid allocation entry specifically may comprise setting this valid allocation entry to 0, thereby obtaining an invalid allocation entry.

The first erasable non-volatile memory particularly may be or may comprise a flash memory. As an example, the flash memory may be or may comprise a flash-EEPROM (electrically erasable programmable read-only memory). The flash-EEPROM specifically may be or may comprise a NAND-flash or a NOR-flash or both. The NAND-flash may be a vertical NAND-flash (V-NAND). The wear leveling may be or may comprise a static wear leveling or a dynamic wear leveling or both. Therein, the static wear leveling is preferred. Other options, however, are feasible.

Generally, the dynamic wear leveling and the static wear leveling may differ in distributing write accesses over the memory. As used herein, the term "dynamic wear leveling" may specifically refer to a wear leveling which distributes a due writing action to a free data block which has suffered the least wear from memory accesses, wherein the free data block may be chosen from of a plurality of data blocks of the memory, wherein each data block of the plurality has been frequently rewritten, i.e. has been rewritten a minimum number of times. Hence, the criterion which determines the plurality of data blocks is referred to as dynamic as it may result in the plurality of data blocks changing over time due to rewriting actions frequently being performed. As further used herein, the term "static wear leveling" may refer to a wear leveling which distributes a due writing action to a free data block which has suffered the least wear from memory accesses, wherein this free data block is typically chosen from a statically predetermined plurality of data blocks. Hence, here the plurality of data blocks from which the free data block is chosen may not change over time. Accordingly, if the plurality of data blocks includes all data blocks of a memory, this may be referred to as static wear leveling.

Each valid data block of the first set preferably has an identifier, and a physical address in the first erasable non-volatile memory. The valid allocation entry for this valid data block of the first set preferably comprises the identifier of the valid data block, and allocated to the identifier, information about the physical address of the valid data block. Preferably the information about the physical address of the valid data block is an offset of a physical address of the valid allocation entry for the valid data block of the first set to the physical address of the valid data block. The first set of valid data blocks specifically may be protected by a CRC-value. The CRC-value, as an example, may have a size of at least 16 bits. Herein, CRC stands for cyclic redundancy check. A cyclic redundancy check may be used to detect accidental changes to data. In this context, a data block into which data is written may get a short check value attached, based on the remainder of a polynomial division of a content of the data. On retrieval of the data, the calculation may be repeated and, in the event the check values do not match, corrective action can be taken against data corruption.

The computer may further comprise a further erasable non-volatile memory. This further erasable non-volatile memory may comprise a block allocation table look up table, comprising a look up allocation entry for each of the valid allocation entries of the block allocation table. Each look up allocation entry may comprise for a corresponding allocation entry, which corresponds to a valid data block: the identifier of the valid data block; and allocated to the identifier of the valid data block information about a physical address of the allocation entry in the block allocation table. Preferably, the information about the physical address of the allocation entry in the block allocation table is an offset of a physical address of the look up allocation entry in the block allocation table look up table to the physical address of the allocation entry in the block allocation table.

The further erasable non-volatile memory specifically may be or may comprise a random access memory (RAM). The application may be designed to trigger a writing of the block allocation table look up table into the further erasable non-volatile memory during or upon booting the computer.

The first erasable non-volatile memory further may comprise a further set of valid data blocks, and a further block allocation table, comprising a valid allocation entry for each valid data block of the further set. Therein, the further set may be redundant to the first set. This means that each valid data block of the further set may have a corresponding identical valid data block in the first set. The further set of valid data blocks may be comprised by the data storage region as well.

The device specifically may not comprise a wear level controller. Therein, a wear level controller may refer to a micro-controller which is configured to perform a wear leveling. As an alternative to a wear level controller, wear leveling may be implemented in software, such as the application of the device according to the invention. Implementing wear leveling in software may, for example, be effected by using special-purpose file systems, such as JFFS2 or YAFFS or both.

The device according to the invention specifically may be or may comprise a mobile device. The mobile device may have a weight or dimensions or both which is/are suitable for the mobile device to be attached to the human or animal body without impairing a mobility of the human or animal. In this context, the device may have a weight of less than 500 g, such as less than 400 g, less than 300 g, less than 200 g, less than 150 g, less than 100 g, less than 70 g, or even less than 50 g. Further, the device may have a length of less than 20 cm, less than 15 cm, or even less than 10 cm. Further preferably, the device may have a thickness of less than 10 cm, less than 7 cm, less than 5 cm, or even than 3 cm.

A device according to the invention may further comprise a pump, such as a medication pump, and a container. The pump specifically may comprise a motor. The container may comprise an active ingredient. The active ingredient specifically may be or may comprise a liquid or may be comprised by a liquid. The active ingredient may be an active pharmaceutical ingredient or an active biological ingredient or both. As an example, the n active biological ingredient may be or may comprise an enzyme. As an example, the enzyme may be or may comprise insulin. An active pharmaceutical ingredient specifically may be or may comprise a drug.

The pump specifically may be arranged and configured for pumping the active ingredient from the container into the human or animal body. The container specifically may have a container volume in the range from 0.5 to 10 ml, such as preferably from 1 to 4 ml, e.g. from 1.2 to 3.5 ml.

The container, as an example, may be at least partially transparent. Therein, the container may comprise a container wall which surrounds a container interior. This container wall may be at least to such an extent transparent to allow for visually checking a fill level of the container from its outside without a need to open the container or to dismount it from the device.

The device may further comprise a hollow needle for injecting the at least one active ingredient subcutaneously into the human or animal body. Hence, the hollow needle may be arranged and configured to conduct the active ingredient, which is pumped by the pump from the container, subcutaneously into the human or animal body. The hollow needle may be connected to the container in a fluid conducting manner. The hollow needle may be attached to the container. The hollow needle specifically may be connected to the container via a fluid conducting connection, wherein the fluid conducting connection, as an example, does not comprise a tube of a length of more than 30 cm, specifically of more than 20 cm, more than 10 cm, more than 5 cm, or even more than 3 cm. As an example, the fluid conducting connection between the hollow needle and the container does not comprise a flexible tube. In this context, the medical action specifically may be or may comprise injecting a portion of the active ingredient into the human or animal body, such as by pumping the portion of the active ingredient from the container via the hollow needle subcutaneously into the human or animal body.

The device may further comprise a first module, and a further module. Therein, the first module may comprise the pump and the container. The further module may comprise a base plate and the hollow needle. Furthermore, the first module or the further module or both may comprise a fixing means. This fixing means may be configured to detachably attach the first module to the further module. This means that via the fixing means the first and the further module may be reversibly attached to and detached from another without destroying any of the first module, the further module and the fixing means. The base plate may comprise a further fixing means, which may comprise an adhesive for attaching the base plate to a skin of the human or animal body. The base plate may comprise a patch having the adhesive for detachably attaching the base plate to a skin of the human or animal body.

The device according to the invention may further comprise a sensor. This sensor may be configured for measuring at least one diagnostic parameter of the human or animal body. The at least one diagnostic parameter generally may be or may comprise any parameter characterizing a body state and/or health state of the human or animal body. As an example, the diagnostic parameter may be or may comprise information on a presence and/or concentration of at least one analyte in the body, such as in a body fluid and/or a body tissue. As an example, the diagnostic parameter may comprise an analyte concentration in a body fluid such as whole blood, interstitial fluid, tear fluid or urine. Additionally or alternatively, another ingredient in the body may be measured, such as one or more ingredients selected from the group consisting of blood cells, an enzyme and a nutrient or a combination of at least two thereof. The nutrient, as an example, may be a carbohydrate or a fat or both. As an example, the ingredient or analyte may comprise carbohydrate such as sugar, e.g. glucose. Consequently, the at least one diagnostic parameter, as an example, specifically may be or may comprise a glucose concentration in whole blood. Other embodiments, however, are feasible.

The device according to the invention specifically may be or may comprise an insulin pump or a continuous glucose sensor or both.

According to a further aspect of the invention, a process comprising as process steps
  a) providing the device according to the invention;
  b) operating the device in consecutive cycles or tasks by using the computer is disclosed. As noted above, the computer may comprise a microprocessor. Further, each cycle or task is characterized by a duration, or a portion of energy, or both. Further, operating the device includes prioritizing the medical action over a cleaning of the first erasable non-volatile memory in terms of the duration, or the portion of energy, or both.

If the device is operate in consecutive tasks in process step b), the duration may be a duration needed to perform the task. Further, the portion of energy may be a portion of energy needed to perform the task.

If the device is operate in consecutive cycles in process step b), the duration may be a duration of the cycle, also referred to as time slot. Further, the portion of energy may be a portion of energy available for the cycle. Each cycle may comprise monitoring a time of the duration left in the cycle, or an energy of the portion of energy left for the cycle, or both. Said monitoring may be effected by the computer, such as by the application. Further, operating the device may include prioritizing the medical action over a cleaning of the first erasable non-volatile memory in terms of the time of the duration left in the cycle or the energy of the portion of energy left for the cycle or both. Moreover, operating the device may include prioritizing a securing of a communication connection of the device over the cleaning of the first erasable non-volatile memory in terms of the time of the duration left in the cycle or the energy of the portion of energy left for the cycle or both. The cleaning of the first erasable non-volatile memory specifically may be called by the wear leveling.

At least one cycle, such as each cycle, may comprise as cycle steps
  a. performing the medical action,
  b. checking if enough time of the duration of the cycle is left or if enough energy of the portion of energy for the cycle is left or both to perform the cleaning of the first erasable non-volatile memory in the cycle.

At least one cycle, such as each cycle, may comprise as further cycle step c. postponing the cleaning of the first erasable non-volatile memory to a further cycle if not enough time of the duration of the cycle is left to perform the cleaning of the first erasable non-volatile memory in the cycle, or not enough energy of the portion of energy for the cycle is left to perform the cleaning of the first erasable non-volatile memory in the cycle, or both. However, if none the preceding three conditions is met the cleaning of the first erasable non-volatile memory is performed in the cycle.

The cycle, such as each cycle, may comprise as further cycle step between the cycle steps a. and b.: a securing of a communication connection of the medical device. The communication connection specifically may be or may comprise a wireless communication connection. This communication connection may be a communication connection between the device and the abovementioned remote controller. The cycle, such as each cycle, may comprise as further cycle step between the cycle steps a. and b.: a writing into the first erasable non-volatile memory.

According to a further aspect of the invention, a use of a wear leveling algorithm, for example a static wear levelling algorithm, and a prioritizing algorithm for storing data in a flash memory of a device for performing at least one medical action at a human or animal body is disclosed. Therein, the prioritizing algorithm is designed to prioritize the medical action over a cleaning of the flash memory called by the wear leveling algorithm. The device may comprise a computer, wherein the computer may comprise the flash memory and an application, wherein the application is configured to control the medical action, wherein the application comprises the prioritizing algorithm or the wear leveling algorithm or both. In the context, the device may be the device according to the invention as described in dew tail above.

According to still another aspect of the invention, a use of the device according to the invention in a treatment of a diabetes mellitus is disclosed. Therein, diabetes mellitus may be of any of the types E10 (type 1 diabetes), E11 (type 2 diabetes), E12, E13 and E14, each according to the classification of ICD-10-WHO version 2016.

The invention further discloses and proposes a computer program including computer-executable instructions for fully or partially performing the process according to the present invention. Specifically, step b) and/or, optionally, step c) of the process may fully or partially be embodied by using computer-executable instructions. Further, the optional component of the process may also fully or partially be embodied by computer-executable instructions. The process may be performed when the program is executed on the computer or on a computer network, preferably on the computer of the device according to the invention. Specifically, the computer program may be stored on a computer-readable data carrier. Thus, the process step b) or c) or both as indicated above may be performed by using a computer or a computer network, preferably by using a computer program. Therein, a preferred computer is the computer of the device according to the invention. A preferred computer program is the application of the device according to the invention.

The invention further discloses and proposes a computer program product having program code means, in order to fully or partially perform the process according to the present invention, such as one or both of steps b) or c), in one or more of the embodiments enclosed herein when the program is executed on a computer or computer network. Specifically, the program code means may be stored on a computer-readable data carrier.

Further, the invention discloses and proposes a data carrier having a data structure stored thereon, which, after loading into a computer or computer network, such as into a working memory or main memory of the computer or computer network, may execute at least one process step of the process according to one or more of the embodiments disclosed herein.

The invention further proposes and discloses a computer program product with program code means stored on a machine-readable carrier, in order to perform at least one process step of the process according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the invention proposes and discloses a modulated data signal which contains instructions readable by a computer system or computer network, for performing at least one process step of the process according to one or more of the embodiments disclosed herein.

Preferably, referring to the computer-implemented aspects of the invention, one or more of the process steps or even all of the process steps of the process according to one or more of the embodiments disclosed herein may be performed by using a computer or computer network. Thus, generally, any of the process steps including provision and/or manipulation of data may be performed by using a computer or computer network. Generally, these process steps may include any of the process steps, typically except for process steps requiring manual work, such as providing the device and/or certain aspects of performing the actual medical action.

Specifically, the present invention further discloses:

A computer or computer network comprising at least one processor, wherein the processor is adapted to perform at least one process step of the process according to one of the embodiments described in this description, a computer loadable data structure that is adapted to perform at least one process step of the process according to one of the embodiments described in this description while the data structure is being executed on a computer, a computer program, wherein the computer program is adapted to perform at least one process step of the process according to one of the embodiments described in this description while the program is being executed on a computer, a computer program comprising program means for performing at least one process step of the process according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing at least one process step of the process according to one of the embodiments described in this description, if the program code means are executed on a computer or on a computer network.

Summarizing the findings of the present invention, the following embodiments are preferred:

Embodiment 1

A device for for performing at least one medical action at a human or animal body; wherein the device comprises an energy source and a computer; wherein the computer
a) comprises a first erasable non-volatile memory, and
b) is configured for performing at least one application, the application being configured
  i) to control the medical action, and
  ii) to prioritize the medical action over a memory cleaning called by a wear leveling.

Embodiment 2

The device according to embodiment 1, wherein the wear leveling is called by a wear leveling algorithm, wherein the wear leveling algorithm is comprised by the application.

Embodiment 3

The device according to embodiment 1 or 2, wherein the prioritizing is called by a prioritizing algorithm, wherein the prioritizing algorithm is comprised by the application.

Embodiment 4

The device according to any of the preceding embodiments, wherein the application is further configured to prioritize a securing of a communication connection of the device over the memory cleaning called by called by the wear leveling.

Embodiment 5

The device according to any of the preceding embodiments, wherein the device is designed to be operated in cycles or tasks, wherein each cycle or task is characterized by a duration, or a portion of energy, or both, wherein the application is designed to prioritize the medical action over the memory cleaning called by the wear leveling in terms of a duration of a cycle or task, or a portion of energy of a cycle or task, or both.

Embodiment 6

The device according to embodiment 5, wherein the device is designed to be operated in cycles, wherein the portion of energy is a portion of energy from the energy source available for the cycle, wherein the application is designed to prioritize the medical action over the memory cleaning called by the wear leveling in terms of a duration of a cycle, or a portion of energy available for a cycle, or both.

Embodiment 7

The device according to embodiment 5, wherein the device is designed to be operated in tasks, wherein the portion of energy is a portion of energy needed to perform the task.

Embodiment 8

The device according to any of embodiments 5 to 7, wherein the device comprises an energy portioning component, wherein the energy portioning component is designed to provide the portion of energy and to be charged by the energy source.

Embodiment 9

The device according to any of the preceding embodiments, wherein the first erasable non-volatile memory comprises
a) a data storage region, comprising a first set of valid data blocks, and
b) a block allocation table, comprising a valid allocation entry for each valid data block of the first set.

Embodiment 10

The device according to embodiment 9, wherein rewriting a valid data block of the first set according to the wear leveling comprises
a) invalidating the valid allocation entry in the block allocation table for the valid data block to be rewritten;
b) writing a further valid allocation entry for a further valid data block of the first set into a free allocation entry of the block allocation table;
c) invalidating the valid data block of the first set to be rewritten, thereby obtaining an invalid data block of the first set; and
d) writing the further valid data block of the first set into a free data block of the data storage region;
wherein if one or both of the following conditions is/are fulfilled the memory cleaning is called:
  A. less than a minimum number of free data blocks is available in the data storage region for step d),
  B. less than a minimum number of free allocation entries is available in the block allocation table for step b);
wherein the memory cleaning comprises erasing a plurality of invalid allocation entries of the block allocation table or a plurality of invalid data blocks of the data storage region or both.

Embodiment 11

The device according to any of the preceding embodiments, wherein the first erasable non-volatile memory is a flash memory.

Embodiment 12

The device according to any of the preceding embodiments, wherein the wear leveling is a static wear leveling.

Embodiment 13

The device according to any of embodiments 9 to 12, wherein each valid data block of the first set has
  a) an identifier, and
  b) a physical address in the first erasable non-volatile memory,
wherein the valid allocation entry for the valid data block of the first set comprises
  a. the identifier of the valid data block, and
  b. allocated to the identifier information about the physical address of the valid data block.

Embodiment 14

The device according to any of embodiments 9 to 13, wherein the first set of valid data blocks is protected by a CRC-value.

Embodiment 15

The device according to any of embodiments 9 to 14, wherein the computer further comprises a further erasable non-volatile memory, wherein the further erasable non-volatile memory comprises a block allocation table look up table, comprising a look up allocation entry for each of the valid allocation entries of the block allocation table.

Embodiment 16

The device according to embodiment 15, wherein each look up allocation entry comprises for a corresponding allocation entry for a valid data block
  a) the identifier of the valid data block, and
  b) allocated to the identifier of the valid data block information about a physical address of the allocation entry in the block allocation table.

Embodiment 17

The device according to embodiment 15 or 16, wherein the further erasable non-volatile memory is a random access memory.

Embodiment 18

The device according to any of embodiments 15 to 17, wherein the application is designed to trigger a writing of the block allocation table look up table into the further erasable non-volatile memory during or upon booting the computer.

Embodiment 19

The device according to any of embodiments 9 to 18, wherein the first erasable non-volatile memory further comprises
  a) a further set of valid data blocks, and
  b) a further block allocation table, comprising a valid allocation entry for each valid data block of the further set,
wherein the further set is redundant to the first set.

Embodiment 20

The device according to any of the preceding embodiments wherein the device does not comprise a wear level controller.

Embodiment 21

The device according to any of the preceding embodiments, wherein the device is a mobile device.

Embodiment 22

The device according to any of the preceding claims, wherein the device further comprises
  a) a pump, and
  b) a container, comprising an active ingredient,
wherein the pump is arranged and configured for pumping the active ingredient from the container into the human or animal body.

Embodiment 23

The device according to embodiment 22, wherein the active ingredient is an active pharmaceutical ingredient or an active biological ingredient or both.

Embodiment 24

The device according to embodiment 22 or 23, wherein the device further comprises a hollow needle, wherein the hollow needle is arranged and configured to conduct the active ingredient pumped by the pump from the container subcutaneously into the human or animal body.

Embodiment 25

The device according to embodiment 24, wherein the device comprises
  a) a first module, and
  b) a further module,
wherein the first module comprises the pump and the container, wherein the further module comprises a base plate and the hollow needle, wherein the first module or the further module or both comprises/comprise a fixing means, wherein the fixing means is configured to detachably attach the first module to the further module.

Embodiment 26

The device according to embodiment 25, wherein the base plate comprises a further fixing means, wherein the further fixing means comprises an adhesive.

Embodiment 27

The device according to any of the preceding embodiments, wherein the device further comprises a sensor, wherein the sensor is configured for measuring a diagnostic parameter of the human or animal body.

Embodiment 28

The device according to any of the preceding embodiments, wherein the device is an insulin pump or a continuous glucose sensor or both.

Embodiment 29

A process, comprising as process steps
  a) providing the device according to any of the preceding embodiments; and
  b) operating the device in consecutive cycles or tasks by using the computer, wherein each cycle or task is characterized by a duration, or by a portion of energy, or both, wherein operating the device includes prioritizing the medical action over a cleaning of the first erasable non-volatile memory in terms of the duration, or of the portion of energy, or both.

Embodiment 30

The process according to embodiment 29, wherein in process step b) the device is operated in consecutive cycles by using the computer,
wherein the portion of energy is a portion of energy available for the cycle,
wherein each cycle comprises monitoring
  i) a time of the duration left in the cycle or
  ii) an energy of the portion of energy left for the cycle or
  iii) both,
wherein operating the device includes prioritizing the medical action over a cleaning of the first erasable non-volatile memory in terms of the time of the duration left in the cycle, or the energy of the portion of energy left for the cycle, or both.

Embodiment 31

The process according to embodiment 29, wherein in process step b) the device is operated in consecutive tasks by using the computer, wherein the portion of energy is a portion of energy needed to perform the task.

Embodiment 32

The process according to any of embodiments 29 to 31, wherein operating the device further includes prioritizing a securing of a communication connection of the device over the cleaning of the first erasable non-volatile memory in terms of the duration, or the portion of energy, or both.

Embodiment 33

The process according to any of embodiments 29 to 32, wherein the cleaning of the first erasable non-volatile memory is called by the wear leveling.

Embodiment 34

The process according to any of embodiments 29 to 33, wherein a cycle comprises as cycle steps
  a. performing the medical action,
  b. checking if enough time of the duration of the cycle is left or if enough energy of the portion of energy for the cycle is left or both to perform the cleaning of the first erasable non-volatile memory in the cycle.

Embodiment 35

The process according to embodiment 34, wherein the cycle comprises as further cycle step
  c. postponing the cleaning of the first erasable non-volatile memory to a further cycle if
    i) not enough time of the duration of the cycle is left to perform the cleaning of the first erasable non-volatile memory in the cycle, or
    ii) not enough energy of the portion of energy for the cycle is left to perform the cleaning of the first erasable non-volatile memory in the cycle, or
    iii) both, and
  if none of i) to iii) is fulfilled performing the cleaning of the first erasable non-volatile memory in the cycle.

Embodiment 36

The process according to embodiment 34 or 35, wherein the cycle comprises as further cycle step between the cycle steps a. and b.: a securing of a communication connection of the medical device.

Embodiment 37

The process according to any of embodiments 34 to 36, wherein the cycle comprises as further cycle step between the cycle steps a. and b.: a writing into the first erasable non-volatile memory.

Embodiment 38

A use of a wear leveling algorithm and a prioritizing algorithm for storing data in a flash memory of a device for performing at least one medical action at a human or animal body, wherein the prioritizing algorithm is designed to prioritize the medical action over a cleaning of the flash memory called by the wear leveling algorithm.

Embodiment 39

The use according to embodiment 38, wherein the device comprises a computer, wherein the computer comprises the flash memory and an application, wherein the application is configured to control the medical action, wherein the application comprises the prioritizing algorithm or the wear leveling algorithm or both.

Embodiment 40

The use according to embodiment 38 or 39, wherein the wear leveling algorithm is a static wear leveling algorithm.

Embodiment 41

A use of the device according to any of embodiments 1 to 28 in a treatment of a diabetes mellitus.

SHORT DESCRIPTION OF THE FIGURES

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.
In the Figures:
FIG. 1A) shows a schematic top view of a device according to the invention;
FIG. 1B) shows a schematic side view of the device according to the invention of FIG. 1A);

FIG. 2 shows a flow chart of a cycle of operating the device according to the invention of the FIGS. 1a) and 1B);

FIG. 3 shows a flow chart of a process according to the invention; and

DETAILED DESCRIPTION OF THE EMBODIMENTS

Figure 1:
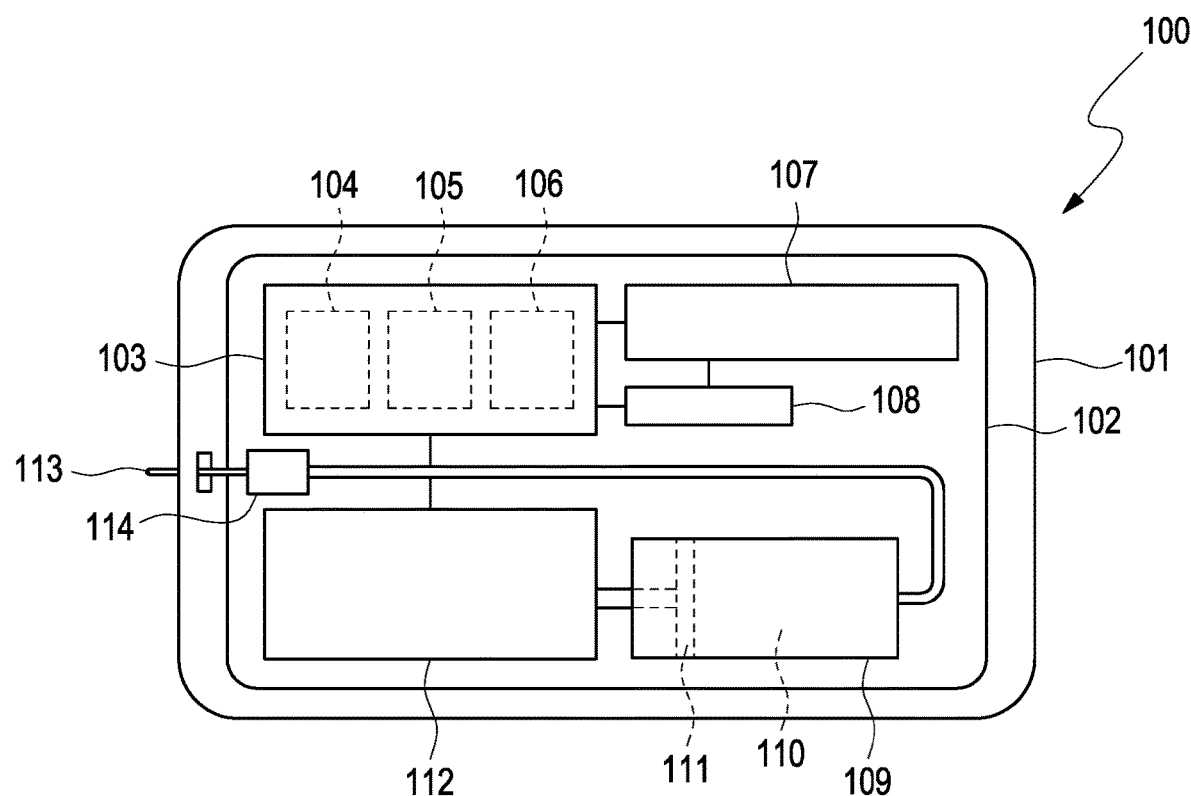
Figure 1:
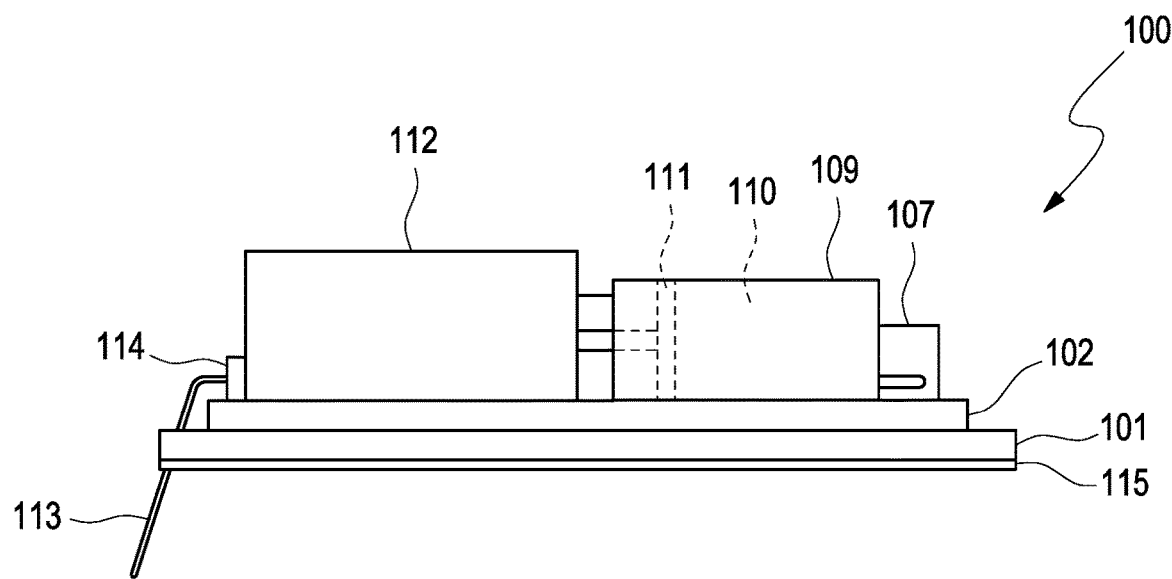

FIG. 1A) shows a schematic top view of a device 100 according to the invention. The device 100 is a mobile insulin pump. Hence, the device 100 is configured for performing a medical action at a human body of a patient. Therein, the medical action may be subcutaneously administering a discrete amount of insulin 110 to the patient, which is also known as bolus, or a quasi continuous amount of insulin, which is known as Basal rate. Accordingly, the device 100 is particularly suitable to be applied in a treatment of type 1 diabetes of the patient. The device 100 comprises a first module 102 and a further module 101, which each comprise counterparts of a fixing means. Using this fixing means, the first 102 and the further module 101 may detachably be attached to one another. The first module 102 comprises a pump, which has a motor 112 and a piston 111. The motor 112 is a step motor. The piston 111 is designed and arranged to act on an active ingredient 110, which is the insulin 110, wherein the insulin is stored in a container 109, which is a transparent pharmaceutical phial. By the motor-driven action of the piston 111, the insulin 110 may be pushed from the container 109 via a pipe into a hollow needle 113 and from there subcutaneously into the patient's body. The first module 102 further comprises an energy source 107, here a battery 107, and a computer 103. The computer 103 comprises a processor 106; a first erasable non-volatile memory 104, which is a flash memory 104; and a further erasable non-volatile memory 105, which is a random access memory (RAM) 105. The first module 102 further comprises an energy portioning component 108, which is a capacitor 108. The further module 101 comprises a base plate 101 and the hollow needle 113. Using an adhesive or patch 115 (shown in FIG. 1B)), the base plate 101 can be attached to the skin of the patient. By releasing the fixing means, the first module 102 can be detached from the further module 101, which may stay attached to the patient's body until the hollow needle 113 needs to be exchanged. Detaching the first module 102 from the further module 101 also comprises releasing a connection between the pipe and the hollow needle 113 via a connector 114. Stored in the RAM 105, there is an application, which is a computer program. The RAM 105 is readable for the processor 106 which can execute the application. Alternatively, the application may be stored in the first erasable non-volatile memory 104. This application is configured to control the medical action and to prioritize the medical action over a memory cleaning of the flash memory 104 called by a wear leveling. The wear leveling is a static wear leveling which is implemented by means of a static wear leveling algorithm into the application. Hence, the device 100 does not comprise a wear leveling controller. Further, the prioritizing is implemented into the application by means of a prioritizing algorithm. In order to allow for the prioritizing, the device 100 is operated in consecutive cycles 200. Therein, each cycle 200 has a duration and a portion of energy from the energy source 107 which is available for the cycle 200. The duration of each cycle 200 is fixed to 1 s. The portion of energy is predetermined by means of the energy portioning component 108. The capacitor 108 is charged with electrical energy from the energy source 107. Each cycle 200 involves depleting the capacitor 108. Therein, the energy which is depleted from the capacitor 108 within a cycle 200 is the portion of energy available for the cycle 200. The prioritizing algorithm of the application prioritizes the medical action over the memory cleaning called by the wear leveling algorithm in terms of the duration of the cycle 200 and the portion of energy available for the cycle 200. Further, the prioritizing algorithm of the application prioritizes writings into the first erasable non-volatile memory 104 over the memory cleaning called by the wear leveling algorithm in terms of the duration of the cycle 200 and the portion of energy available for the cycle 200. Details of the prioritizing are discussed in the context of FIG. 2 below. Details of the wear leveling are discussed in the context of FIG. 4 below.

FIG. 1B) shows a schematic side view of the device 100 according to the invention of FIG. 1A). In FIG. 1B) the adhesive or patch 115 is depicted.

FIG. 2 shows a flow chart of a cycle 200 of operating the device 100 according to the invention of the FIGS. 1A) and 1B). Operating the device 100 in consecutive cycles 200 as described below, incorporates the prioritizing algorithm as mentioned in the context of FIG. 1A). During each cycle 200, the time of the duration left in the cycle 200 as well as the energy of the portion of energy left for the cycle 200 is continuously monitored by the application. Each cycle 200 comprises the following steps. At the beginning of each cycle 200 a medical action is performed—step 201. The medical action may be administering insulin 112 in form of a bolus or a Basal rate. Therein, the application calls the medical action. In consequence, the processor 106 activates the pump which starts the bolus. Further, a communication control is performed in step 203. Therein, the application checks if a communication connection is intact. If not, the application tries to re-establish the connection, otherwise an error message is communicated. In step 202, the application checks if important data needs to be written into the flash memory 104. Examples of important data are any data about the status of the device 100, such as the amount of insulin 110 left in the container 109 or the fuel level of the battery 107. In step 210, this important data is written. In step 204 a further pump control action is performed. Here, the application may check if enough insulin 110 is left in the container 109 according to the important data written before. In a further step 205 the application checks if a memory cleaning according to the wear leveling algorithm is due. If not, no more action is performed in this cycle 200 and the application waits for the cycle 200 to end—step 209. After the duration of the cycle 200 has lapsed the next cycle 200 is started. If the memory cleaning is due, the application calls the memory cleaning and checks if enough energy is left from the portion of energy available for the pending cycle to perform the memory cleaning—step 206. If not, no more action is performed in this cycle 200 and the application waits for the cycle 200 to end step 209. If there is enough energy left, the application checks if enough time of the duration of the cycle 200 is left to perform the memory cleaning within the cycle 200—step 207. If there is not enough time left, no more action is performed in this cycle 200 and the application waits for the cycle 200 to end—step 209. If there is enough time left, the memory cleaning is performed 208. Afterwards, the application waits for the cycle 200 to end, before the next cycle 200 starts.

FIG. 3 shows a flow chart of a process 300 according to the invention. The process comprises a process step a) 301 of providing the device 100 according to the FIGS. 1A) and 1B). In a following process step b) 302 the device 100 is operated in consecutive cycles 200 as described above in the contexts of the FIGS. 1A), 1B) and 2.

Figure 4:
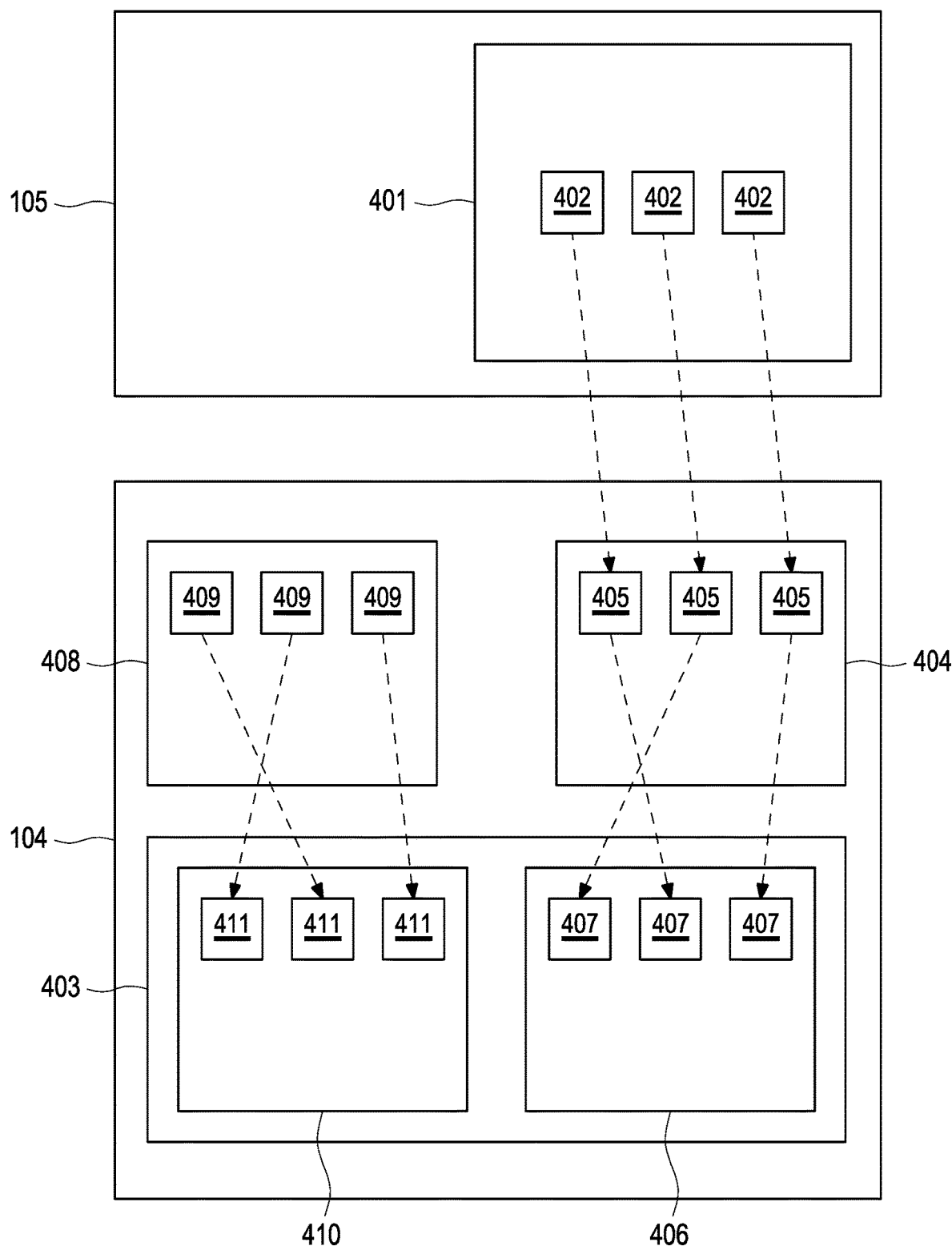
FIG. 4 shows a schematic view of a memory architecture of the device according to the invention of the FIGS. 1A) and 1B).

FIG. 4 shows a schematic view of a memory architecture of the device 100 according to the invention of the FIGS. 1A) and 1B). The FIG. 4 shows the first erasable non-volatile memory 104, which is the flash memory 104. This flash memory 104 comprises a data storage region 403 which comprises a first set of valid data blocks 406. The flash memory 104 further comprises a block allocation table 404 which comprises a valid allocation entry 405 for each valid data block 407 of the first set 406. In the FIG. 4 the valid data blocks 407 of the first set 406 are connected to their corresponding valid allocation entries 405 in the block allocation table 404 by dashed arrows. Rewriting a valid data block 407 of the first set 406 according to the wear leveling algorithm comprises: invalidating the valid allocation entry 405 in the block allocation table 404 for the valid data block 407 to be rewritten; writing a further valid allocation entry for a further valid data block of the first set 406 into a free allocation entry of the block allocation table 404; invalidating the valid data block 407 of the first set 406 to be rewritten, thereby obtaining an invalid data block of the first set 406; and writing the further valid data block of the first set 406 into a free data block of the data storage region 403. If no free data block is available in the data storage region 403 for writing the further valid data block of the first set 406, or no free allocation entry is available in the block allocation table 404 for writing the further valid allocation entry, or both the wear leveling algorithm calls for the memory cleaning of the flash memory 104. Therein, the memory cleaning comprises erasing all invalid allocation entries of the block allocation table 404 and all invalid data blocks of the data storage region 403. FIG. 4 also shows the further erasable non-volatile memory 105, which is the RAM 105. This RAM 105 comprises a block allocation table look up table 401, comprising a look up allocation entry 402 for each of the valid allocation entries 405 of the block allocation table 404. The application is designed to create the block allocation table look up table 401 in the RAM 105 from the block allocation table 404 during each booting of the computer 103. By using the block allocation table look up table 401 access to the flash memory 104 for reading can be performed faster. In the FIG. 4 the look up allocation entries 402 of the block allocation table look up table 401 are connected to their corresponding valid allocation entries 405 of the block allocation table 404 by dashed arrows. The flash memory 104 further comprises a further set of valid data blocks 410 in the data storage region 403, and a further block allocation table 408, comprising a valid allocation entry 409 for each valid data block 411 of the further set 410. Therein, the further set 410 is redundant to the first set 406. This means that the further set 410 is an identical copy of the first set 406. In the FIG. 4 the valid data blocks 411 of the further set 410 are connected to their corresponding valid allocation entries 409 in the further block allocation table 408 by dashed arrows. Using the redundant further set 410 and its further block allocation table 408 allows for an improved error detection and error correction.

LIST OF REFERENCE NUMBERS 100 device according to the invention
101 base plate/further module
102 first module
103 computer
104 first erasable non-volatile memory/flash memory
105 further erasable non-volatile memory/RAM
106 processor
107 energy source/battery
108 energy portioning component/capacitor
109 container
110 active ingredient/insulin
111 piston
112 motor
113 hollow needle
114 connector
115 adhesive/patch
200 cycle
201 perform medical action
202 check if writing of important data is due
203 communication control
204 further pump control action
205 check if memory cleaning is due
206 check if enough energy is left for memory cleaning
207 check if enough time is left for memory cleaning
208 perform memory cleaning
209 wait for next cycle
210 writing of important data
y yes
n no
300 process according to the invention
301 process step a)
302 process step b)
401 block allocation look up table
402 look up allocation entry
403 data storage region
404 block allocation table
405 valid allocation entry of the block allocation table
406 first set of valid data blocks
407 valid data block of the first set
408 further block allocation table
409 valid allocation entry of the further block allocation table
410 further set of valid data blocks
411 valid data block of the further set

The invention claimed is:

1. A device for performing at least one medical action at a human or animal body;
   wherein the device comprises an energy source and a computer;
   wherein the computer
      a) comprises a first erasable non-volatile memory, and
      b) is configured for performing at least one application, the application being configured
         i) to control the medical action,
         ii) to prioritize the medical action over a memory cleaning called by a wear leveling, and
         iii) to prioritize a securing of a communication connection of the device over the memory cleaning called by the wear leveling.

2. The device according to claim 1, wherein the wear leveling is called by a wear leveling algorithm,
   wherein the wear leveling algorithm is comprised by the application.

3. The device according to claim 1, wherein the prioritizing is called by a prioritizing algorithm,
   wherein the prioritizing algorithm is comprised by the application.

4. The device according to claim 1, wherein the device is designed to be operated in cycles or tasks, wherein each cycle or task is characterized by a duration, or a portion of energy, or both, wherein the application is designed to prioritize the medical action over the memory cleaning called by the wear leveling in terms of a duration of a cycle or task, or a portion of energy of a cycle or task, or both.

5. The device according to claim 4, wherein the device is designed to be operated in cycles, wherein the portion of energy is a portion of energy from the energy source available for the cycle, wherein the application is designed to prioritize the medical action over the memory cleaning called by the wear leveling in terms of a duration of a cycle, or a portion of energy available for a cycle, or both.

6. The device according to claim 4, wherein the device comprises an energy portioning component, wherein the energy portioning component is designed to provide the portion of energy and to be charged by the energy source.

7. The device according to claim 1, wherein the first erasable non-volatile memory comprises
   a) a data storage region, comprising a first set of valid data blocks, and
   b) a block allocation table, comprising a valid allocation entry for each valid data block of the first set.

8. A device for performing at least one medical action at a human or animal body:
   wherein the device comprises an energy source and a computer;
   wherein the computer
   a) comprises a first erasable non-volatile memory comprising a data storage region, comprising a first set of valid data blocks, and a block allocation table comprising a valid allocation entry for each valid data block of the first set, and
   is configured for performing at least one application, the application being configured
      i) to control the medical action, and
      ii) to prioritize the medical action over a memory cleaning called by a wear leveling,
   wherein rewriting a valid data block of the first set according to the wear leveling comprises
      a) invalidating the valid allocation entry in the block allocation table for the valid data block to be rewritten;
      b) writing a further valid allocation entry for a further valid data block of the first set into a free allocation entry of the block allocation table;
      c) invalidating the valid data block of the first set to be rewritten, thereby obtaining an invalid data block of the first set; and
      d) writing the further valid data block of the first set into a free data block of the data storage region;
   wherein if one or both of the following conditions is/are fulfilled the memory cleaning is called:
   A. less than a minimum number of no free data blocks is available in the data storage region for step d),
   B. less than a minimum number of free allocation entries is available in the block allocation table for step b);
   wherein the memory cleaning comprises erasing a plurality of invalid allocation entries of the block allocation table or a plurality of invalid data blocks of the data storage region or both.

9. The device according to claim 7, wherein the computer further comprises a further erasable non-volatile memory,
   wherein the further erasable non-volatile memory comprises a block allocation table look up table, comprising a look up allocation entry for each of the valid allocation entries of the block allocation table.

10. The device according to claim 7, wherein the first erasable non-volatile memory further comprises
    a) a further set of valid data blocks, and
    b) a further block allocation table, comprising a valid allocation entry for each valid data block of the further set,
    wherein the further set is redundant to the first set.

11. The device according to claim 1 wherein the device does not comprise a wear level controller.

12. A use of a wear leveling algorithm and a prioritizing algorithm for storing data in a flash memory of a device for performing at least one medical action at a human or animal body,
    wherein the prioritizing algorithm is designed to prioritize the medical action over a cleaning of the flash memory called by the wear leveling algorithm.

13. A use of the device according to claim 1 in a treatment of a diabetes mellitus.

14. A process, comprising as process steps
    a) providing the device according to any of the preceding claims; and
    b) operating the device in consecutive cycles or tasks by using the computer,
    wherein each cycle or task is characterized by a duration, or by a portion of energy, or both,
    wherein operating the device includes prioritizing the medical action over a cleaning of the first erasable non-volatile memory in terms of the duration, or of the portion of energy left, or both.

* * * * *